(12) United States Patent
Fischer et al.

(10) Patent No.: US 10,251,695 B2
(45) Date of Patent: Apr. 9, 2019

(54) SURGICAL INSTRUMENT WITH TISSUE RECOGNITION

(71) Applicant: ERBE ELEKTROMEDIZIN GMBH, Tuebingen (DE)

(72) Inventors: Klaus Fischer, Nagold (DE); Alexander Neugebauer, Moessingen (DE); Dominik Spether, Freiburg (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 356 days.

(21) Appl. No.: 14/308,830

(22) Filed: Jun. 19, 2014

(65) Prior Publication Data

US 2014/0378961 A1    Dec. 25, 2014

(30) Foreign Application Priority Data

Jun. 20, 2013    (EP) .................................... 13173012

(51) Int. Cl.
| | |
|---|---|
| A61B 18/12 | (2006.01) |
| A61B 5/00 | (2006.01) |
| A61B 18/00 | (2006.01) |
| A61B 18/14 | (2006.01) |

(52) U.S. Cl.
CPC ........ *A61B 18/1233* (2013.01); *A61B 5/0075* (2013.01); *A61B 18/1485* (2013.01); *A61B 2018/00642* (2013.01); *A61B 2018/00904* (2013.01)

(58) Field of Classification Search
CPC ............ A61B 18/1233; A61B 18/1485; A61B 2018/00642; A61B 2018/00904; A61B 5/0075
See application file for complete search history.

(56) References Cited

U.S. PATENT DOCUMENTS

| | | | | |
|---|---|---|---|---|
| 4,981,138 A | * | 1/1991 | Deckelbaum | A61B 5/0071 600/477 |
| 5,769,791 A | * | 6/1998 | Benaron | A61B 5/0086 600/473 |
| 6,066,102 A | * | 5/2000 | Townsend | A61B 10/06 600/104 |
| 6,852,109 B2 | * | 2/2005 | Winston | A61B 18/1492 606/41 |
| 6,869,430 B2 | * | 3/2005 | Balbierz | A61B 18/1206 606/41 |
| 7,108,690 B1 | * | 9/2006 | Lefki | A61B 18/203 606/10 |
| 8,518,094 B2 | * | 8/2013 | Wang | A61N 5/06 607/89 |
| 9,060,750 B2 | | 6/2015 | Lam | |

(Continued)

FOREIGN PATENT DOCUMENTS

| | | | |
|---|---|---|---|
| EP | 2 514 380 A1 | 10/2012 | |
| WO | WO 2011/055369 A2 | 5/2011 | |

*Primary Examiner* — Daniel W Fowler
(74) *Attorney, Agent, or Firm* — Blank Rome LLP

(57) ABSTRACT

An electrosurgical device for recognizing tissue by means of spectral analysis of the light generated at an electrode. An acoustic or optical indicator device displays the tissue type permanently or when detecting certain tissue. Indicators, in particular optical indicators, are arranged in the application field of view, so as to support the user in response to making an incision.

12 Claims, 6 Drawing Sheets

(56) References Cited

U.S. PATENT DOCUMENTS

| | | | |
|---|---|---|---|
| 2002/0016533 A1* | 2/2002 | Marchitto | A61B 5/0066 600/310 |
| 2002/0019644 A1* | 2/2002 | Hastings | A61B 17/22 606/159 |
| 2005/0014995 A1* | 1/2005 | Amundson | A61B 1/018 600/105 |
| 2006/0013454 A1* | 1/2006 | Flewelling | G06K 9/4652 382/128 |
| 2006/0116669 A1* | 6/2006 | Dolleris | A61B 18/203 606/17 |
| 2007/0270792 A1* | 11/2007 | Hennemann | A61B 5/0059 606/41 |
| 2007/0287998 A1* | 12/2007 | Sharareh | A61B 18/1492 606/41 |
| 2008/0051773 A1* | 2/2008 | Ivanov | A61N 5/0616 606/12 |
| 2008/0221409 A1 | 9/2008 | Hoarau | |
| 2008/0262489 A1* | 10/2008 | Steinke | A61B 18/1492 606/33 |
| 2008/0312673 A1* | 12/2008 | Viswanathan | A61B 90/36 606/159 |
| 2010/0016855 A1* | 1/2010 | Ramstein | A61B 1/00105 606/49 |
| 2012/0116379 A1* | 5/2012 | Yates | A61B 17/00234 606/33 |
| 2012/0259231 A1* | 10/2012 | Tsubouchi | A61B 5/0059 600/477 |

* cited by examiner

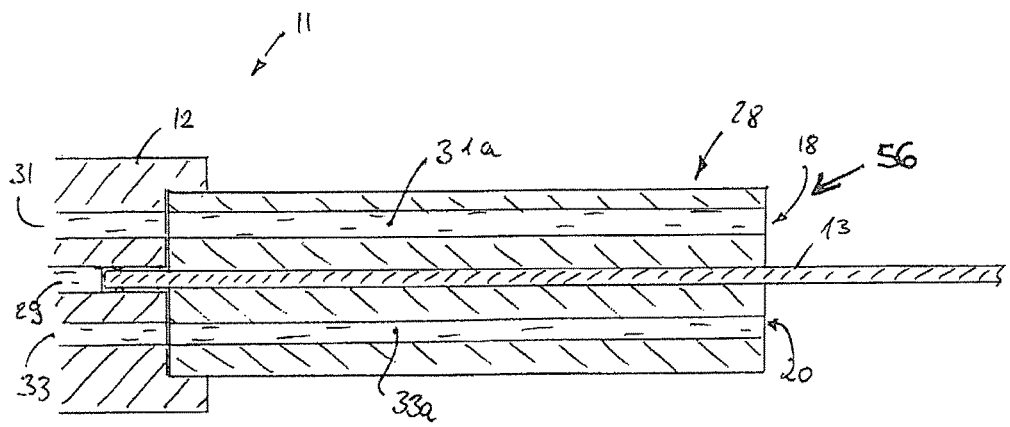
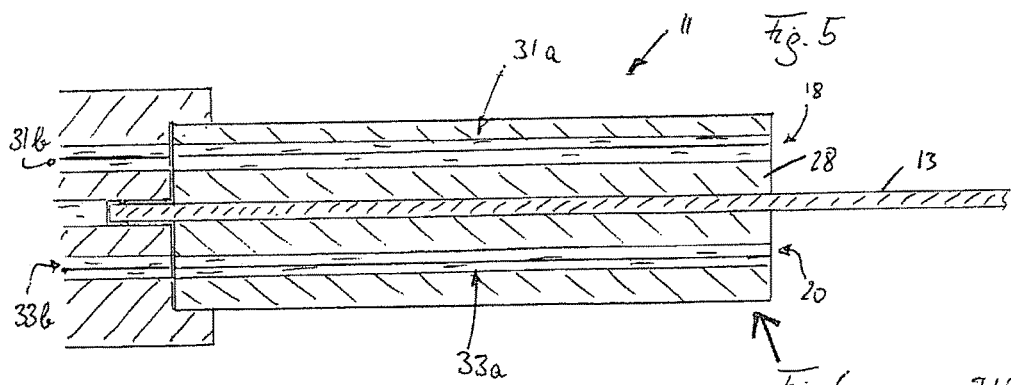
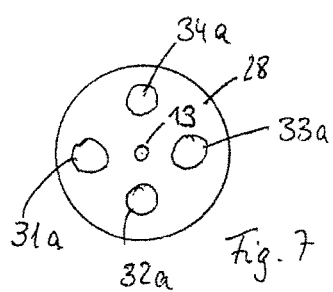
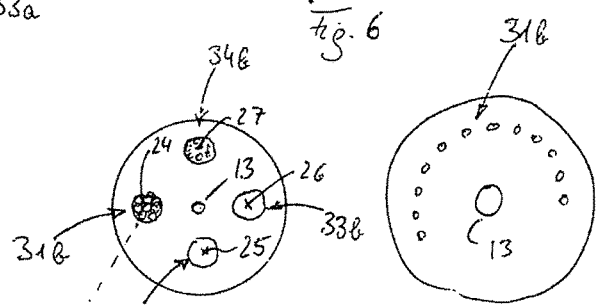
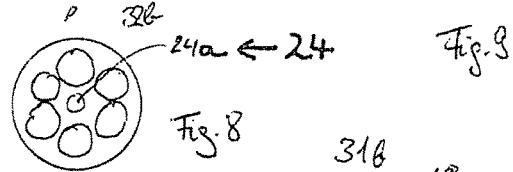
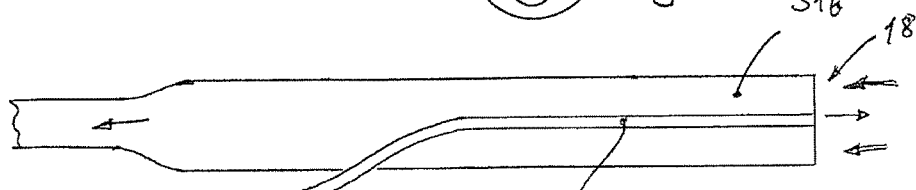
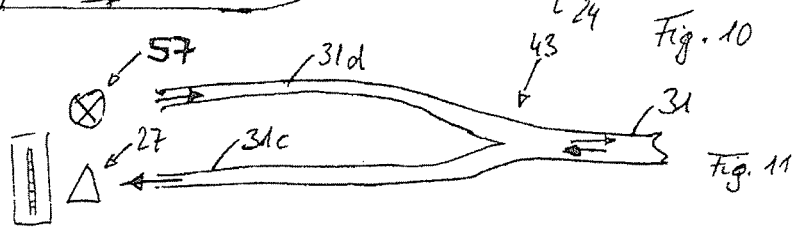

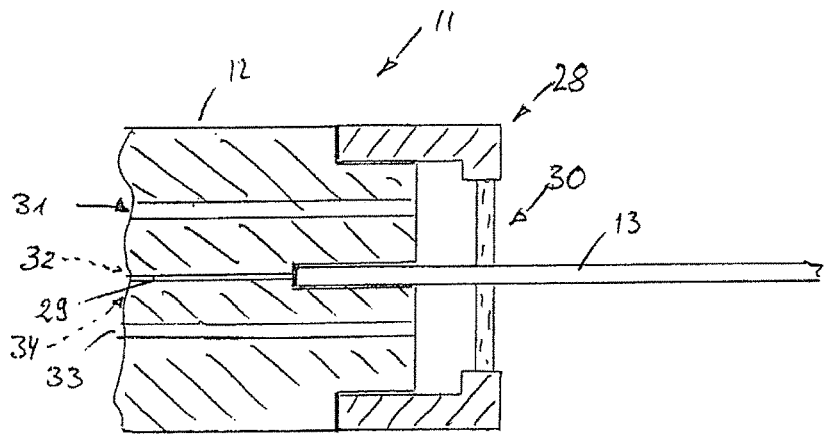
Fig. 12
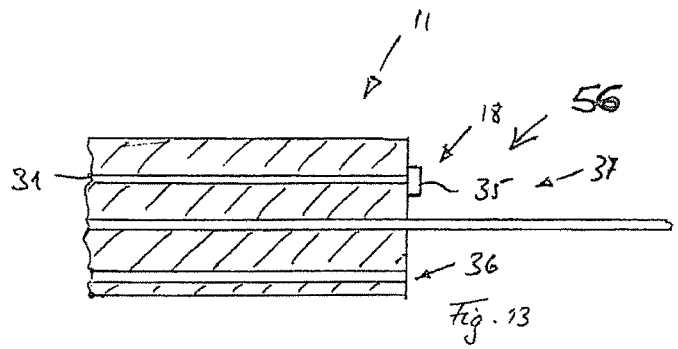
Fig. 13
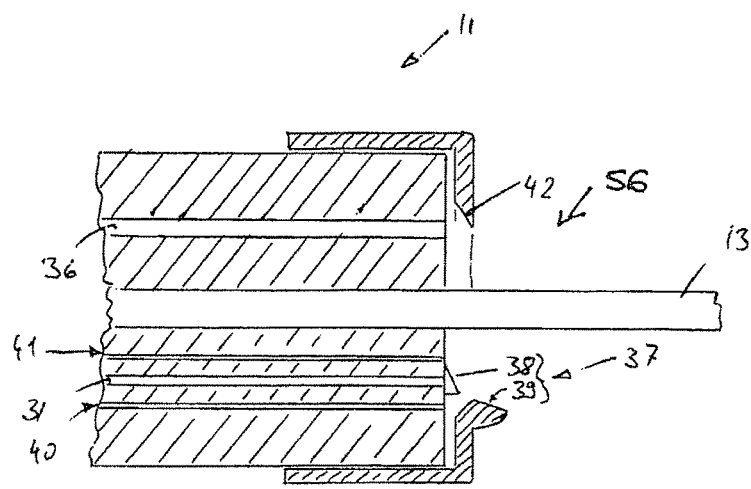
Fig. 14
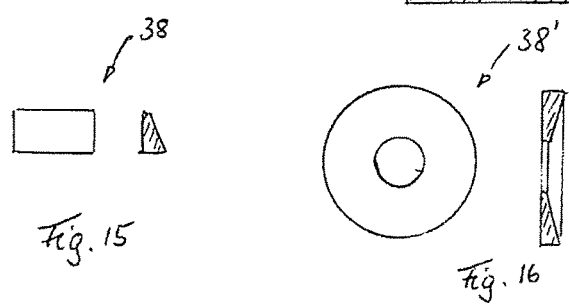
Fig. 15
Fig. 16

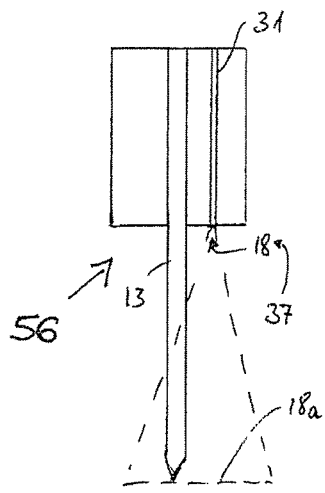
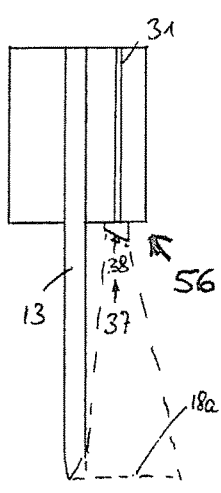
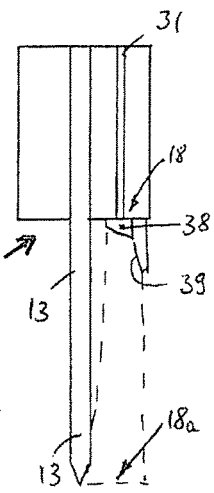
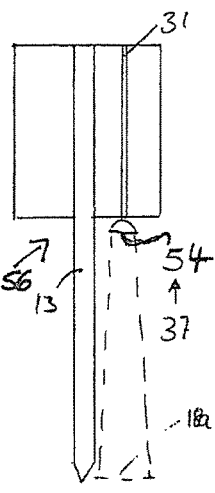
Fig. 17  Fig. 18  Fig. 19  Fig. 20
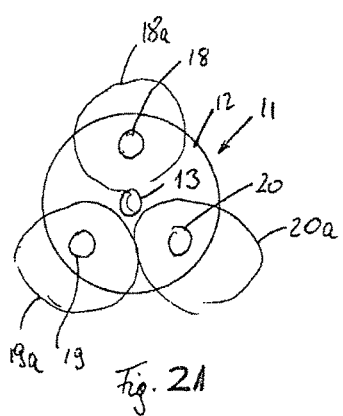
Fig. 21
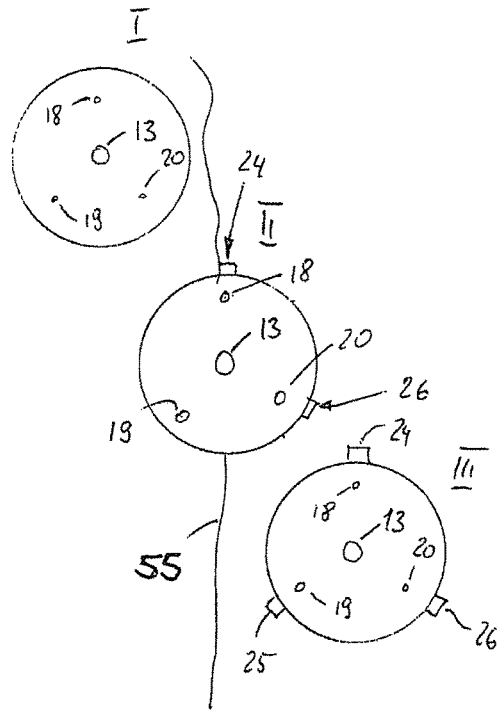
Fig. 22

SURGICAL INSTRUMENT WITH TISSUE RECOGNITION

TECHNICAL FIELD

Embodiments of the invention relate to an electrosurgical device for recognizing tissue type.

BACKGROUND

The plasma ablation by means of HF power, which is guided to an electrode, for removing plaque in blood vessels is known from WO 2011/055369. The corresponding instrument is inserted into the blood vessel and creates a HF spark at its distal end, which acts on plaque or also on other biological material, such as blood. The created light is supplied to an optical spectrometer, which, by means of the presence or absence of the typical phosphor spectral line, provides information, whether living cells or plaque are dissolved by the spark.

On principle, it is thus possible for the user to concentrate the surgical action to certain biological structures, here the plaque, by means of corresponding machine support, and to preserve other tissue.

SUMMARY

It is an object of the disclosed embodiments to provide an improved orientation to the user in response to the use of HF surgical instruments.

An electrosurgical device according to the disclosed embodiments comprises an instrument comprising an electrode, which can be connected to an electric source. The instrument can be embodied as monopolar or bipolar instrument for open surgery. Likewise, it can be embodied as laparoscopic monopolar or bipolar instrument. It thus encompasses at least one electrode, which can be fed with HF power. A second electrode, which closes the circuit, can be a neutral electrode, which is to be fastened to the patient, or a second electrode at the instrument.

The device includes a light-recording device, which is preferably arranged so as to be stationary relative to the electrode, that is, it is provided with said electrode at an instrument. The at least one (first) light-recording device defines a first light-recording field, which detects at least a portion of the spark generated by the electrode. The light-recording device is connected to a light-analysis device, for example via an optical fiber or an optical fiber bundle, to determine tissue characteristics by means of spectral analysis. The light-analysis device is equipped to compare characteristics of the recorded spectrum with reference data and to derive a statement therefrom, whether the electric discharge, that is the HF spark, e.g., is in contact with a certain tissue type or is not in contact with it. This information is provided to an indicator device. The indicator device can be embodied as acoustic indicator device. For this purpose, it can encompass a one-sound or multi-sound signaling device. The latter can be arranged at the instrument, e.g. at the handle thereof, or also at the feeding device (HF generator), at the light-analysis device or it can be embodied as separate signaling device. Such a signaling device can be connected to the light-analysis device via cables or via a wireless transmission path.

Preferably, the indicator device is embodied as optical indicator device comprising optical indicators. Preferably, this indicator device is arranged such that the optical signal, which is to be perceived by the user, is located in the application field of view, that is, in an area, which is visible by the user during the application.

In the case of a surgical instrument for open surgery, the indicator device can be formed by means of one or a plurality of indicators in the form of lamps at the handle of the instrument, for example at its distal end. In the case of an instrument for open surgery as well as in the case of a laparoscopic instrument, the indicator device can, as an alternative, encompass light outlet windows, which project light onto the tissue, which is touched by the electrode. In the case of a laparoscopic instrument, the indicator device can furthermore or in the alternative be equipped to superimpose corresponding information into an image, which is perceived by the user, for example on video glasses or on a screen. The display can be made by means of different luminous colors, by means of different symbols or by means of the position of colors or symbols on a projected area. The projected area can be the biological tissue or a video screen. For displaying the tissue characteristics, the indicator device can display different luminous colors, for example green light in the case of normal tissue, red light in the case of tumor tissue or blue light in the case of unknown tissue.

The light can be guided onto the application field by means of optical fibers and can thus provide the user with an easy orientation.

The basic principles, which have been described in this respect, can be realized by means of an instrument, which only encompasses one light-recording device and thus only a (first) light-recording field. However, the device is preferably provided with a second light-recording device, which defines a second light-recording field, which differs from the first light-recording field. It is thus not only possible to obtain information relating to the characteristics of the tissue, which is affected by the electric discharge, at the instrument, but information can also be obtained relating to the direction of the position of a tissue boundary relative to the electrode. For example, the light-recording fields can be defined such that they encompass their central point in different directions, viewed from the electrode. The light-recording fields can thereby be embodied so as to overlap one another or, as it is preferred, so as not to overlap one another. Different appearances of light, which appear in different zones of the HF spark and which are based on the contact of the spatially expanded HF spark with two different tissue types, can thus be detected simultaneously or subsequently, and directional information can be derived therefrom. Said directional information can serve the purpose of activating or deactivating different indicators, which are located in the field of view of the user. The activation or deactivation can be the lighting up or the fading of the indicators or a color change thereof or can take place by displaying or non-displaying, respectively, of symbols.

To determine tissue characteristics by means of spectral analysis, the light analysis-device compares the spectrum supplied by the tissue with a reference spectral dataset. Preferably, the reference spectral dataset is obtained in one or in a plurality of calibration steps. A calibration step is preferably carried out with a reduced current at known tissue. For example, an HF spark comprising a tissue type, which is of interest, for example healthy tissue and/or also diseased tissue, can be generated at the onset of the application by means of current, which is so low that even though an appearance of light is created, a surgical effect does not happen. It is ensured with this that the calibration, that is, the recording of at least one reference spectral dataset is carried out without damaging tissue.

The instrument according to the disclosed embodiments can encompass light outlet windows and light inlet windows. For example, the light outlet windows can be formed by means of distal ends (front surfaces) of optical fibers, which serve to output signals, while the light inlet windows are formed by the distal ends (front surfaces) of optical fibers, which serve to record light. The light-absorbing and light-emitting fibers can be arranged in one or a plurality of strands or bundles. A cleaning device can be assigned to the light inlet windows (and/or light outlet windows). Said cleaning device can be formed by means of nozzles for the escape of cleaning fluids, that is, liquids or gases. The gas or liquid stream, which escapes from these nozzles, e.g. parallel to the cutting electrode, can serve to control the temperature of the light outlet and/or inlet windows, so as to prevent a condensation as well as the adhesion of tissue. Preferably, a valve for the controlled release of the gas or fluid stream is accommodated in spatial vicinity of the gas outlet nozzle or nozzles, e.g. in the handle of the instrument. The valve can be connected electrically or mechanically to an activation switch, which serves to electrically activate the electrode. To release the fluid, provision can be made for a lead time and for a follow-up time, so as to ensure that the fluid stream is present in the desired intensity, as soon as and as long as the electrode is activated.

At its distal end, the instrument can encompass a removable part, which is provided for only a one-time use, while the remaining instrument can be sterilized and is provided for repeated use. For this purpose, the electrode is held on a coupling piece, which is releasably connected to the instrument. In addition, the coupling piece encompasses at least one viewing window, which can be arranged in a ring-shaped manner around the electrode, for example. This applies both for the laparoscopic instruments as well as for instruments for open surgery.

Preferably, the light-analysis device encompasses an operational control device, which is equipped to start the spectral tissue analysis only if the light-analysis device detects a defined spectral characteristic. The defined spectral characteristic can be, for example, that the detected spectrum lies within a predetermined tolerance band. The operational control device can thus recognize, whether the recorded light stems from biological tissue or from an electric discharge, which is in contact therewith, respectively. In contrast, the operational control device recognizes a spark, which is not in contact with biological tissue, or an ambient light as being irrelevant and thus does not trigger a tissue display. In this manner, the device according to the disclosed embodiments can be offered as retrofitting device for existing electrosurgical devices. An electrical connection between the power-supply device is not required.

Further details of advantageous embodiments of the invention are the subject matter of the description, of the claims or of the drawings.

BRIEF DESCRIPTION OF THE DRAWINGS

FIG. 5 shows an embodiment of the instrument, in schematized sectional longitudinal sectional illustration;

FIG. 6 shows a modified embodiment of the instrument according to FIG. 2, in a schematized sectional longitudinal sectional illustration;

FIG. 7 shows the instrument according to FIG. 5 in a schematized front view;

FIG. 8 shows the instrument according to FIG. 6 in a schematized front view;

FIG. 9 shows a modified embodiment of an instrument, in schematized front view;

FIG. 10 shows a fiber arrangement for transmitting and receiving fibers for the instrument according to FIG. 8 or 9;

FIG. 11 shows a fiber coupler for joining or separating, respectively, transmitting and receiving optical fibers for an instrument according to FIG. 7;

FIG. 12 shows an instrument comprising a particularly reduced coupling piece, which is provided for a one-time use, in schematized, longitudinally cut illustration;

FIG. 13 shows a particularly simple version of an instrument, in a schematized longitudinally cut sectional illustration;

FIG. 14 shows a modified embodiment of an instrument comprising light-recording device, in schematized sectional longitudinal sectional illustration;

FIGS. 15 and 16 show different prism arrangements at the light-recording device to define the light-recording field;

FIGS. 17 to 20 show different embodiments of light-recording devices at instruments for defining different light windows;

FIG. 21 shows light-recording fields at an instrument comprising three light-recording devices;

FIG. 22 shows the instrument in three different positions relative to a tissue boundary, schematically illustrating the corresponding display or indication, respectively;

DETAILED DESCRIPTION

Figure 1:
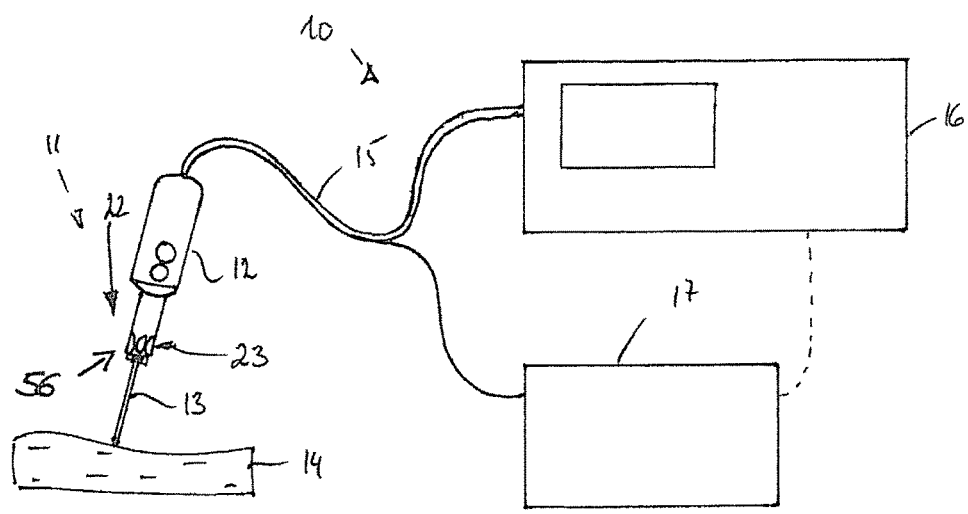
FIG. 1 shows a schematic illustration of a device.

FIG. 1 illustrates a device 10 for electrosurgery in a schematic manner. The device 10 includes an instrument 11 comprising a handle 12 and an electrode 13 for acting on the tissue 14. The instrument 11 is connected to a power-supply device 16, for example in the form of an HF generator, via a cable 15. In addition, the cable 15, or a part thereof, leads to a light-analysis device 17, by means of which light, which is created at the electrode 13 by means of electrical discharge, is analyzed to determine the tissue type of the tissue that is touched. For this purpose, the light-analysis device 17 performs a spectral analysis of the light, which is generated in the HF spark of the electrode 13. This light is recorded via a light-recording device 56, which comprises at least one, but preferably a plurality of light inlet windows 18, 19, 20, 21, which are arranged in the vicinity of the electrode 13, for example around it. The light recorded via the light inlet windows 18 to 21 is supplied to the light-analysis device 17, for example by means of optical fibers arranged in the cable 15, and is analyzed spectrally. The spectral analysis serves to identify the tissue type and to generate corresponding signals, which are preferably output via an indicator device 23, which is arranged in the application field of view 22. The application field of view is thereby that area in the vicinity of the handle 12 and of the electrode 13 that is visible by the user during the use, and which lies within the field of vision of the user during the use.

The indicator device 23 makes it possible to display a performed tissue analysis quickly and with a high informative value directly at the patient, for example during an electrosurgical procedure, thus providing the possibility of differentiating tissues during an on-going use.

Figure 2:
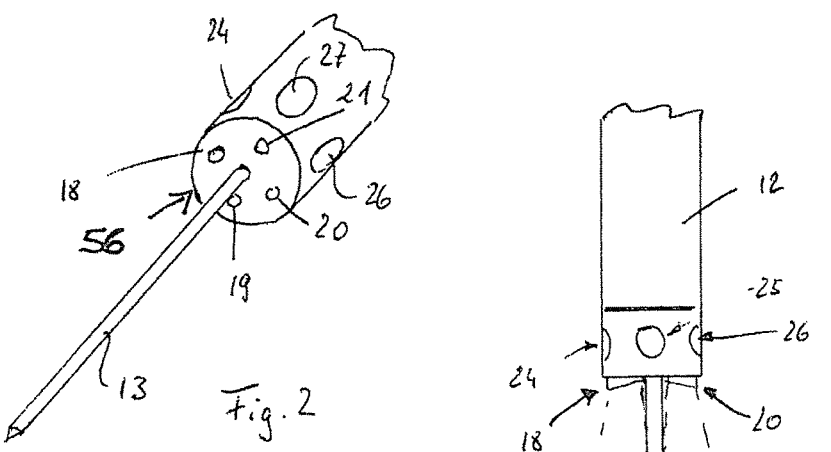
FIG. 2 shows the instrument from FIG. 1 in a schematized sectional perspective illustration.
Figure 3:
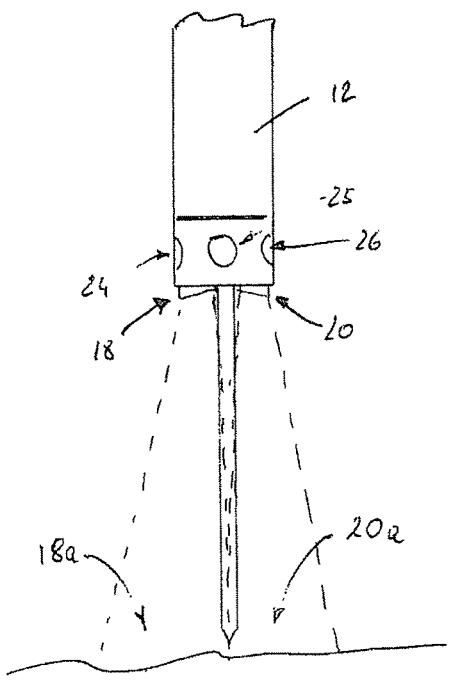
FIG. 3 shows the instrument according to FIG. 2 in a schematized side view.
Figure 4:
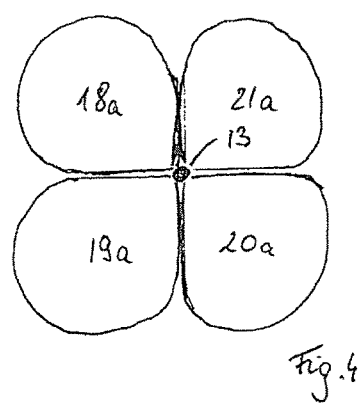
FIG. 4 shows the light-detection field of the instrument according to FIG. 2, in schematized illustration.

As is illustrated in FIGS. 1 and 2, the indicator device 23 can comprise a plurality of indicators 24 to 27 (see also FIG. 8), via which a light signal is emitted, for example, so as to provide the user with an orientation. In the case of an instrument 11 comprising only a single light inlet window 18 and a connected light-analysis device 17, this can already take place in that the indicators 24 to 27 (the number thereof is not important herein) emit a signal, for example, when a tissue is encountered that differs from the tissue in which an incision is to be performed. This can be signaled by means of illumination, color change or the like. In the case of embodiments that encompass two or more light inlet windows 18 to 21, directional information can additionally be created. For this purpose, FIG. 3 illustrates the obtaining of directional information by defining various light-recording fields 18a, 20a of the light inlet windows 18 and 20. FIG. 4 illustrates the different light-recording fields 18a, 19a, 20a, 21a of the four light inlet windows 18, 19, 20, 21 in top view. They group around the electrode 13 and overlap one another as little as possible or not at all. Via corresponding light-guiding means, every light-recording window 18 to 21 is connected to the light-analysis device 17, which analyzes the individual light spectrums recorded by the light inlet windows 18 to 21 either in parallel or cyclically one after the other via a multiplexer, and compares them with a tissue spectrum, which was recorded ahead of time or which was obtained from a database (or to a plurality of obtained tissue spectrums or tissue spectrums, which were stored ahead of time).

In one embodiment, four tissue spectrums are recoded in this manner for the four light-recording windows 18 to 21a and are compared continuously to one or a plurality of reference spectrums. Accordingly, an indicator of the indicators 24 to 27 can light up or show a color change when coming into contact with a tissue that does not correspond to the tissue designated for the incision. Directional information and thus an orientation aid for the use is thus provided to the user in a particularly comfortable manner.

A two-part embodiment of the instrument 11 is illustrated in FIG. 5, in the case of which an exchangeable coupling piece 28 is arranged at the handle 12. Said coupling piece supports the electrode 13, which is in contact with a line 29 via a corresponding plug contact device. The coupling piece 28 can encompass one or a plurality of fiber-optic light guides 31a, 33a, which couple to the optical fibers 31, 33. The distal ends of the fiber-optic light guides 31a, 33a form the light inlet windows 18 and 20 and are part of the light-recording device 56. FIG. 7 illustrates the arrangement comprising four fiber-optic light guides 31a to 34a.

As is illustrated in FIGS. 6 and 8, provision can also be made instead of for a monofilament optical fiber 31 to 34 for a fiber bundle 31b to 34b in each case, into which indicator fibers 24a can be embedded, which form the indicators 24, 25, 26, 27. The distal ends of the indicator fibers of the fiber bundles 31b to 34b, which end in the light outlet windows, are part of the light-recording device 56. The indicators 24, 25, 26, 27 serve the purpose of projecting the tissue indication into the field of view of the user and thus form projection means. The detailed view of FIG. 8 illustrates this. It is clarified that the light inlet window 18 is formed herein by a ring of individual fibers, which are arranged around a fiber, which serves as indicator 24. The indicator 24 is to serve the purpose of projecting colored light, for example, to the corresponding light-recording field 18a, so as to mark the tissue type. The light, which originates from this light-recording field 18a and which is generated by the HF spark, is recorded via the light inlet windows and is supplied to the analysis. The fiber-optic light guides 31a, 33a of the coupling piece 28, which are illustrated in FIG. 6, can be embodied accordingly. However, it is also possible herein to provide for a coupling piece 28 according to FIG. 5. In addition, the individual fibers of a fiber bundle 31b can be arranged in a pitch circle-shaped manner, according to the model of FIG. 9, for example. Other arrangements are possible to obtain symmetrical or asymmetrical light-recording fields.

It is also possible to guide the light, which serves to indicate tissue and which is guided into the light-recording window, and the light, which originates from the HF spark, in a single optical fiber 31, as is illustrated in FIG. 11. At a location, which is located at a distance from the light inlet window 18, which is to be imagined on the right-hand side in FIG. 11, provision can be made for a fiber coupler 43, which is formed by means of a Y-branching of the optical fiber 31. While a first part 31c of the optical fiber 31 leads to the light analyzer 17, a second part 31d of the optical fiber 31 leads to a source 57, which supplies the indicator 24 with a signal, preferably a light signal. The light analyzer 17 is illustrated schematically in FIG. 11 by means of a prism for light diffraction and schematically by means of a line scan camera.

The design of the instrument 11 can be varied in a variety of ways. For example, as is shown in FIG. 12, the instrument 11 can encompass a coupling piece 28 at its distal end, which supports the electrode 13 which is designated for the one-time use. It can be attached to the distal end of the instrument 11 as a cap and can be connected thereto. The electrode 13 thereby comes into electrical contact with the line 29 for electrical power, in particular HF voltage. Provision can be made around the electrode 13 for a viewing window 30, so as to allow light of the spark, which was created at the electrode 13, to reach one or a plurality of optical fibers 31 to 34. For example, the optical fibers 31 to 34 can be connected to the light inlet windows 18 to 21.

The coupling piece 28 comprising the electrode 13 and the window 30 represents a disposable product. The handle 12, in contrast, can be reused and can be sterilized accordingly.

FIG. 13 illustrates a modified embodiment of the instrument 11 comprising a light-recording device 56 comprising one or a plurality of light inlet windows 18. A silicon cushion 35, which serves to reduce the reflection losses caused by the adaptation of the refraction indexes at the contact point of the optical fibers, is in contact with the optical fiber 31 at the distal end. In addition, provision can be made in the case of this embodiment, as well as in the case of all other embodiments, for a cleaning device, for example in the form of a fluid channel 36. The latter serves to supply (liquid or gaseous) fluid to the distal end of the instrument 11 and thus serves to prevent contaminations of the silicon cushion 35 or of any other light inlet window 18 to 21 by smoke particles, aerosol and pieces of tissue, which are created during the electrosurgical use and which would otherwise be able to deposit on the front surface of the optical fiber 31 or of other elements, which form n lens 37 of any kind. As such, provision is made in the embodiment according to FIG. 13 only for the silicon cushion 35. However, as illustrated in FIG. 14, the lens 37 can also include a prism 38, which is arranged at the distal end of the optical fiber 31, so as to focus the light-recording field to a certain area of the electrode 13. Optionally, the lens 37 can include one or a plurality of further elements, such as a mirror 39, for example, which is arranged laterally at a radial distance to the electrode 13 and to the prism 38. As is shown in FIG. 19, said mirror can serve the purpose of concentrating the light-recording field 18a to a narrow area, which is adjacent to the electrode 13. In the case of embodiments comprising only one light inlet window 18 as well as in the case of embodiments comprising several of such light inlet windows, provision can be made for such a lens arrangement. As is further illustrated in FIG. 14, provision can be made around the optical fiber 31 in a ring-shaped arrangement for one or a plurality of fluid channels 40, 41, so as to generate a fluid jet, for example a gas jet, so as to keep the lens 37 clean. The fluid channels 40, 41 can be arranged independent from the fluid channel 36. A deflection nozzle 42 can be assigned to the fluid channel 36, so as to guide the jet, which escapes from the channel 36, radially inwardly. The distal end of the fluid channel 36, 40, 41, the silicon cushion 35 and the lens 37 are also part of the light-recording device 56.

The fluid channels 36, 40 and/or 41 are connected to a source (e.g. pump or compressed gas container), which is not illustrated in detail, for pressurized fluid. To regulate or to at least block and release the fluid stream, provision is made for one or a plurality of valves. They are preferably arranged in the handle 12, so as to turn the fluid stream on and off without a delay, if possible. The valve (or the valves, respectively), can be connected mechanically or electrically to an activation switch for the HF activation, which, e.g., can also be arranged at the handle. Provision can be made between the activation switch, the HF generator and the valves for a delay block, which ensures that the HF activation only takes place when the fluid stream has been established as desired.

In the case of this embodiment, a wedge prism 38 according to FIG. 15 can be used or a ring prism 38', which is arranged concentrically around the electrode 13 and which is illustrated separately in FIG. 16 in cross section and in top view. The mirror surface 39 serves to deflect the recorded light to the light inlet window, which is formed herein by means of the front surface of the optical fiber 31. A large light output is obtained through this. The deflection nozzle 42 serves to clean the lens 37. It deflects the fluid stream radially inwardly, so that the lens 37 is protected well against dirt, wherein the fluid stream, however, is not guided directly onto the tissue surface. Irritations of the generated spark as well as dangers, such as gas embolisms, can be avoided through this. The additional fluid channel 40, 41, which can be embodied as coaxial splitting channel, additionally protects the wedge prism 38 as well as the mirror surface 39 from contaminations.

While the embodiment of the instrument 11 according to FIG. 14 is illustrated schematically in FIG. 19, FIGS. 17, 18 and 20 show other embodiments, in the case of which provision can optionally also be made for channels 36, 40, 41 according to the above description.

In the case of the embodiment according to FIG. 17, the viewing window 18 is formed by means of the end of the optical fiber 31. The light-recording field 18a detects the entire extent of the electrode 13. The light, which emanates from the spark of the electrode 13, is thus detected independent on which radial direction of the electrode 13 the tissue is located. The lens 37 is formed herein only by means of the virtually punctiform aperture of the optical fiber 31.

In the case of the embodiment according to FIG. 18, the prism 38 belongs to the lens 37, so that a light-recording window 18a comprising a changed, for example reduced size, is created. With regard to the electrode 13, the light-recording field 18a is located only on one side thereof. A significant asymmetry is created through this, so that mainly the light, which is created in FIG. 18 to the right of the electrode 13, is recorded. This embodiment can form the basis for instruments, which define a plurality of light-recording windows 18a to 21a, as is illustrated in FIG. 4.

As is shown in FIG. 20, the lens 37 can encompass a collimating lens 54, which is arranged upstream of the distal end of the optical fiber 31. The collimator lens or a different suitable lens system can be located in a lens holder, which is not illustrated in detail, which can be embodied so as to be replaceable, for example. In addition, provision can be made for the deflection nozzle, which has already been explained in context with FIG. 14. The collimator lens 54 can be used to generate a virtually parallel light beam travel, so as to specifically obtain a small light-recording field 18a and thus specifically the light-recording from certain areas of the HF spark or from another electrical discharge. The deflection nozzle can again be used to protect the optical fiber 31 and/or the collimator lens 54 from contamination, without guiding the fluid stream to the tissue surface.

Figure 23:
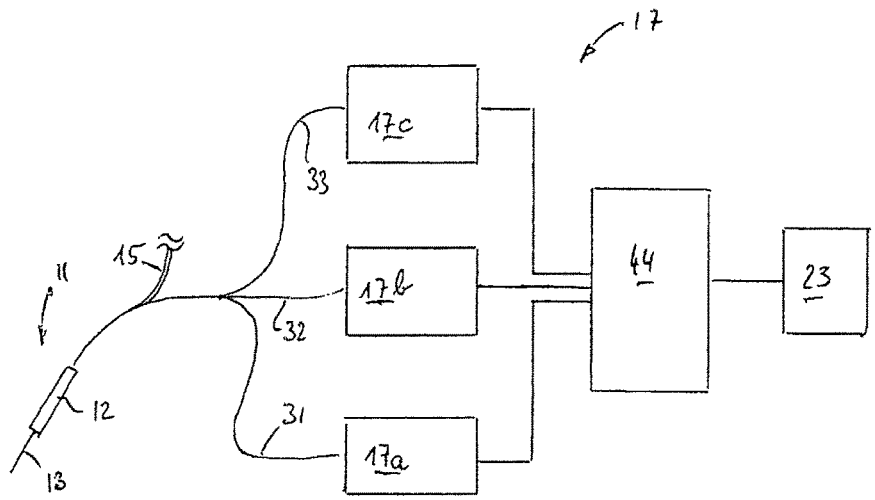
FIG. 23 shows the basic structure of the light-analysis device as block diagram.

FIG. 23 illustrates the system architecture of the light analyzer 17. The part of the line 15, which leads to the light analyzer 17, comprises a plurality of optical fibers 31, 32, 33, which in each case belong to different light inlet windows and which thus guide light from different sides of the electrode 13 to the light analyzing device 17. The latter comprises one, two or a plurality of light analyzers 17a, 17b, 17c, which in each case affect a spectral analysis of the recorded light. For this purpose, they can encompass grating spectrometers or photodiode arrays. As illustrated in FIG. 1, the light-analysis device 17 can be arranged as external device or also integrally in the handle 12 of the instrument 11. A photodiode array consists of at least two, preferably of a plurality of photodiodes, which are in each case sensitive for a suitable wavelength range. A spectral signal, which is more or less finely screened, can thus be generated for the received light. Said spectral signal is supplied to a processing device 44, which is connected downstream and which controls the indicator device 23.

Figure 24:
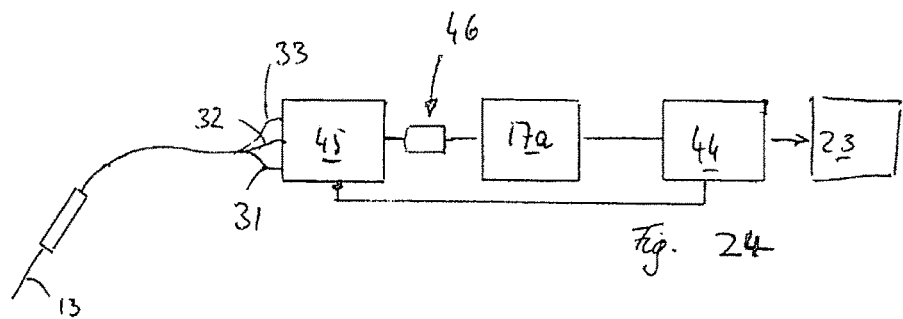
FIG. 24 shows the basic structure of a modified embodiment of a light-analysis device.

Instead of this arrangement comprising three light analyzers, the arrangement according to FIG. 24 can also encompass a single light analyzer 17a, to which a multiplexer 45 and, if applicable, an intensity increasing device 46 are connected upstream. The multiplexer 45 can be controlled by the processing device 44, so as to consecutively analyze the light of the individual optical fibers 31, 32, 33 in a specific manner. This arrangement is suggested in particular when provision is made for a large number of light inlet windows, which look at different areas of a spark. The intensity increasing device 46 is a coupling device, for example, which is directed to minimizing light loss, for example in that light is distributed optimally to the inlet gap of a spectrometer. This can take place by means of a geometric adaptation of the arriving optical fiber from a round cross section to a flat cross section. If a fiber bundle is used instead of a monofilament optical fiber 31, this can be affected by means of splicing the fiber bundle. In the alternative, a suitable focusing optics can be used, which comprises cylinder lenses, for example.

Figure 25:
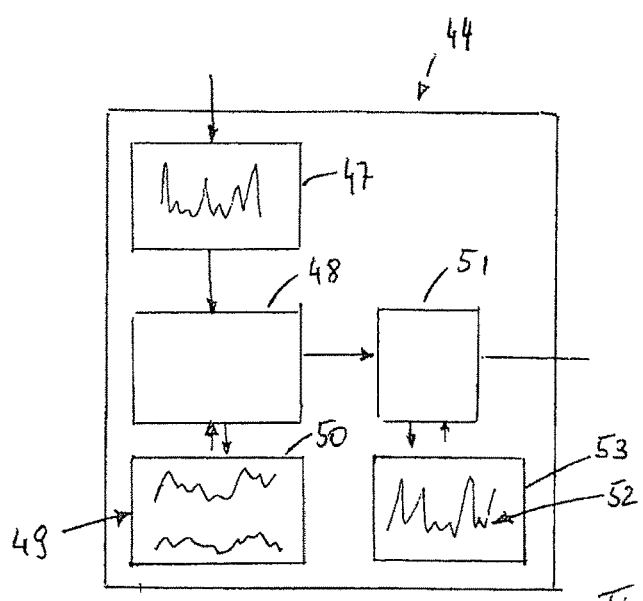
FIG. 25 shows the basic structure of a processing device for light analysis comprising an operational control device for starting and stopping the tissue analysis.

FIG. 25 illustrates the mode of operation of the processing device 44 and thus of the programming thereof. At its input, the processing device 44 records the spectrum 47. The latter is present in the form of suitable electrical signals, that is, data. This spectrum was recorded at a light inlet window 18. A comparator block 48 forms an operational control device. It compares the spectrum 47 with predetermined spectral characteristics 49, which are provided in a memory block 50 for being recalled. The spectral characteristics 49 can be the predetermined sizes or size range of spectral lines or of spectral ranges. They are determined such that they only appear, if the HF spark is in contact with biological tissue via the electrode 13. The spectral characteristics are defined such that they do not occur in HF sparks, for example, which burn in the air or against metal parts, or in ambient light. For example, the yellow sodium line or the ratio thereof to the other light intensity can serve to do so.

Figure 26:
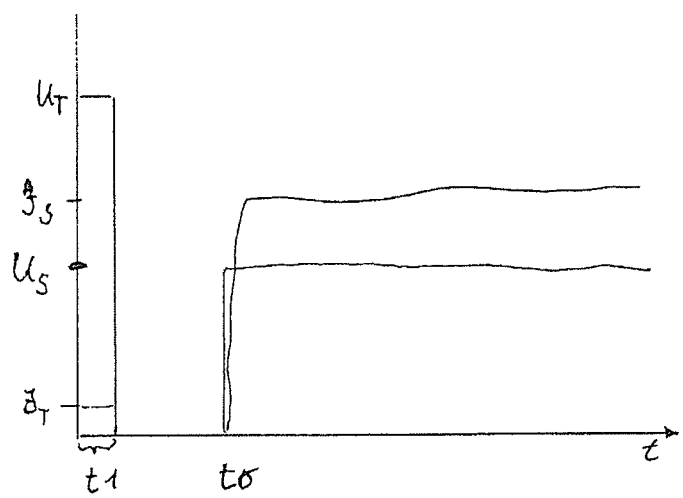
FIG. 26 shows time diagrams for visualizing a calibration with a reduced surgical effect.

If the comparator block 48 determines that certain characteristics of the recorded light correspond to the spectral characteristics 49, it provides the recorded spectrum 49 to the analysis block 51 for further analysis. Analysis block 51 now compares the spectrum 47 with one or a plurality of reference spectrums 52, which are present in the form in corresponding reference datasets. They can originate from a database, for example, or can have been determined at the beginning of the application or also ahead of time. FIG. 26 illustrates the recording thereof. For example, a test spark is ignited in a first time period t1. A high voltage $U_T$, yet a low current $I_T$ can thereby be used, for example to avoid undesirable surgical effects. For example, a reference spectrum of healthy tissue can be recorded at the time period t1. In the alternative or in addition, a test spark can be generated at a different tissue at a further time period, also with an increased voltage $U_T$ and reduced current $I_T$, and a further reference spectrum can be recorded. This can take place at malignant tissue, for example.

At a later time period tσ, a use can be carried out with a lower voltage $U_S$, yet with a higher current $I_S$ and thus with the desired surgical effect. The operation can thereby take place as illustrated in FIGS. 25 and 26.

FIG. 21 illustrates an instrument 11 comprising three light inlet windows 18, 19, 20, which define three light-recording windows 18a, 19a, 20a, which are arranged around the electrode 13. The light recorded at that location is analyzed in the light-analysis device 17 according to FIGS. 23 to 25.

In a position I in FIG. 22, the electrode 13 is located in healthy tissue. The light-recording windows 18, 19, 20 detect light, which the HF spark, which was generated at the electrode 13, generates in healthy tissue and the reference spectrum of which is present as reference dataset 53. Initially, the compactor block 48 recognizes that operation is carried out in biological tissue and thus releases the spectral analysis. The analysis block 51 recognizes the incision in the healthy tissue, so that the indicator device 23 is not activated.

In the next position II, the electrode 13 reaches a tissue boundary 55 between the known tissue type and a different tissue type, for example malignant tissue, for which a reference dataset is not present. While light, which originates from a spark or spark part, respectively, which was generated only in healthy biological tissue, is still recorded via the light inlet window 19, the light inlet windows 18 and 20 record light, which originates from sparks or spark parts, respectively, which were generated in other types of tissue, for example in malignant tissue. The analysis bock 51 recognizes the non-correspondence with the reference dataset accordingly and activates the indicators 24, 26. If the incision is guided further in the direction of malignant tissue (or other foreign or unknown tissue), the electrode 13 has finally arrived completely in this tissue. Light, which does not correspond to the reference spectrum, is now recorded via all three light inlet windows 18, 19, 20. All of the indicators 24, 25, 26 accordingly signal the deviation from the tissue, which is typified in the calibration step.

It is also possible to operate with a plurality of reference datasets, for example in that a first reference dataset is recorded for healthy tissue and a second reference dataset is recorded for malignant tissue. In this case, each of the indicators can provide information, for example, by lighting up and/or by changing color, for example green for healthy tissue, red for malignant tissue and a further color, for example blue for unknown tissue.

As suggested in FIGS. 2 and 3, these signals can be made by means of indicators on the handle 12 or in or on the coupling piece 28 as well as by deflection into the respective light-recording fields 18a to 20a and are thus located in the field of view of the user.

In the case of an electrosurgical device 10 for use at biological tissue, tissue, which was typified ahead of time, is recognized by means of a spectral analysis of the light, which is generated at the electrode 13. An acoustic or optical indicator device 23 displays the tissue type permanently or in response to the detection of certain tissues. Indicators, in particular optical indicators 24 to 27, are arranged in the application field of view, so as to support the user when making an incision.

What is claimed as new and desired to be protected by Letters Patent of the United States is:

1. An electrosurgical device for impacting a biological tissue by means of an electrical discharge comprising:
   an instrument comprising an electrode, which can be connected to an electrical source;
   a plurality of light-recording devices arranged radially around the electrode and oriented in an axial direction toward respective portions of biological tissue to record in respective light-recording fields light emitted from a spark hitting the respective portions of biological tissue, the light-recording fields extending from the plurality of light-recording devices to the portions of biological tissue and arranged radially around the electrode;
   a light-analysis device configured to determine tissue type of the portions of biological tissue by means of spectral analysis of the light emitted by the spark and recorded by the light-recording devices; and
   an indicator device for displaying a color corresponding to the determined tissue type and for indicating the radial direction relative to the electrode of the portions of the biological tissue having the respective tissue type,
   wherein the indicator device comprises projection means to project the colored light corresponding to the determined tissue type into the light-recording fields.

2. The device of claim 1, wherein the indicator device is arranged in an area that is visible by a user of the electrosurgical device.

3. The device of claim 1, wherein the light-analysis device is equipped to compare the recorded light with at least one reference spectral dataset.

4. The device of claim 3, wherein the light-analysis device is configured to obtain the reference spectral dataset in one or a plurality of calibration steps.

5. The device of claim 1, wherein the projection means includes indicator fibers or a second part of an optical fiber, which are connected to a plurality of light outlet windows.

6. The device of claim 5, wherein the light outlet windows are respectively arranged in or at a plurality of light inlet windows of respective light-recording devices.

7. The device of claim 1, wherein each of the plurality of light-recording devices includes distal end areas of at least one fiber bundle extending from a respective light inlet window to the light-analysis device.

8. The device of claim 1, wherein each of the plurality of light-recording devices comprises a light inlet window, to which a cleaning device is assigned.

9. The device of claim 1, wherein each of the plurality of light-recording devices includes a lens arrangement.

10. The device of claim 1, wherein the electrode is held at a coupling piece releasably connected to the instrument, wherein the coupling piece comprises a plurality of viewing windows corresponding respectively to the plurality of light-recording devices that are arranged around the electrode in a ring-shaped manner.

11. The device of claim 1, wherein the light-analysis device comprises an operational control device, which is equipped to start the spectral tissue analysis as soon as the light-analysis device detects a predetermined spectral characteristic.

12. The device of claim 1, wherein the light-recording fields do not overlap one another.

* * * * *